(12) United States Patent
Hauck

(10) Patent No.: US 6,560,489 B2
(45) Date of Patent: May 6, 2003

(54) THERAPEUTIC DEVICE AND METHOD FOR TREATING DISEASES OF CARDIAC MUSCLE

(75) Inventor: John A. Hauck, Shoreview, MN (US)

(73) Assignee: EM Vascular, Inc., Shoreview, MN (US)

(*) Notice: Subject to any disclaimer, the term of this patent is extended or adjusted under 35 U.S.C. 154(b) by 88 days.

(21) Appl. No.: 09/756,567

(22) Filed: Jan. 8, 2001

(65) Prior Publication Data

US 2001/0031986 A1 Oct. 18, 2001

Related U.S. Application Data

(63) Continuation-in-part of application No. 09/638,233, filed on Aug. 14, 2000, now abandoned.
(60) Provisional application No. 60/143,510, filed on Aug. 24, 1999.

(51) Int. Cl.[7] ................................................. A61N 1/08
(52) U.S. Cl. ................................................. 607/62; 607/2
(58) Field of Search ................................ 607/1, 2, 4, 5, 607/9, 14, 10, 72, 75, 62, 67

(56) References Cited

U.S. PATENT DOCUMENTS

| | | | |
|---|---|---|---|
| 3,745,995 A | 7/1973 | Kraus | 128/82.1 |
| 3,890,953 A | 6/1975 | Kraus et al. | 128/1.5 |
| 3,915,151 A | 10/1975 | Kraus | 128/1.5 |
| 4,266,532 A | 5/1981 | Ryaby et al. | 128/1.5 |
| 5,320,642 A | 6/1994 | Scherlag | 607/9 |
| 5,334,222 A | 8/1994 | Salo et al. | 607/17 |
| 5,401,233 A | 3/1995 | Erickson et al. | 600/14 |
| 5,433,735 A | 7/1995 | Zanakis et al. | 607/50 |
| 5,450,859 A | 9/1995 | Litovitz | 128/897 |
| 5,544,665 A | 8/1996 | Litovitz et al. | 128/897 |
| 5,566,685 A | 10/1996 | Litovitz et al. | 128/898 |
| 5,634,899 A | 6/1997 | Shapland et al. | 604/51 |
| 5,782,873 A | 7/1998 | Collins | 607/2 |
| 5,800,528 A | 9/1998 | Lederman et al. | 623/3 |
| 5,855,570 A | 1/1999 | Scherson et al. | 604/304 |
| 5,968,527 A | 10/1999 | Litovitz | 424/400 |
| 6,200,259 B1 | 3/2001 | March | 600/9 |
| 6,240,314 B1 | 5/2001 | Plicchi et al. | 607/14 |
| 6,263,242 B1 | 7/2001 | Mika et al. | 607/25 |
| 6,363,279 B1 * | 3/2002 | Ben-Haim et al. | 607/9 |

FOREIGN PATENT DOCUMENTS

| | | | |
|---|---|---|---|
| WO | WO 97/25098 | 7/1997 | A61N/1/00 |
| WO | WO 98/10830 | 3/1998 | A61N/1/362 |
| WO | WO 99/03533 | 1/1999 | A61N/1/362 |
| WO | WO 00/27466 | 5/2000 | A61N/1/00 |

OTHER PUBLICATIONS

Spinale, Francis G., et al., entitled "Myocardial matrix degradation and metalloproteinase activation in the failing heart: a potential therapeutic target" from Cardiovascular Research, vol. 46, #2, May 2000, pp. 225–238.

Kanno, Shinichi, et al., entitled "Establishment of a Simple and Practical Procedure Applicable to Therapeutic Angiogenesis" from Circulation 1999; 99: 2682–2687.

* cited by examiner

Primary Examiner—George R. Evanisko
(74) Attorney, Agent, or Firm—Thomas J. Nikolai; Nikolai & Mersereau, P.A.

(57) ABSTRACT

An apparatus and method for conferring a therapeutic current to the heart is provided. The apparatus includes a first electrode, a second electrode, a current generator and a controller. The apparatus may further include a sensor. The sensor is generally configured to measure field strength between the first and second electrode. The sensor may also monitor the cardiac cycle. The method includes applying an electric stimulus to the heart and sensing the electric field generated by the electric stimulus to prevent the level of current from inducing unwanted depolarization.

10 Claims, 4 Drawing Sheets

THERAPEUTIC DEVICE AND METHOD FOR TREATING DISEASES OF CARDIAC MUSCLE

CROSS-REFERENCE TO RELATED APPLICATIONS

This application is a continuation-in-part of U.S. patent application Ser. No. 09/638,233, filed Aug. 14, 2000 now abandoned, which claims priority from U.S. Provisional Application Ser. No. 60/143,510, filed Aug. 24, 1999. The above-referenced Patent and Provisional Applications are incorporated by reference in the present application in their entirety.

BACKGROUND OF THE INVENTION

1. Field of the Invention

The present invention relates to an apparatus and method for treatment of the heart and, more particularly, to an apparatus and method for providing a therapeutic sub-threshold electrical current to the heart.

2. Discussion of the Related Art

A wide range of therapies is available for the treatment of cardiac tissue damage, heart failure and for treatment of the specific underlying disease processes. Most of these therapies may be classified as drugs, surgical intervention, or cardiac assist devices. The cardiac assist devices assist the heart in pumping function to relieve the heart of stresses during the healing process. If a condition is caused by coronary disease or is exacerbated by conduction defects, available therapies include either bypass surgery or angioplasty in the case of the former, or pacemaker therapy in the case of the latter. The above-mentioned damage and diseases as well as other factors set in motion the condition known as congestive heart failure (CHF). Although therapies have addressed treating specific indications, few therapies address the problem of tissue remodeling.

Tissue remodeling refers to the histological alteration of tissue over time. Remodeling may include histological and/or biochemical changes at the tissue, cellular and molecular levels. Tissue remodeling can be either beneficial or degenerative to a patient. Tissue remodeling is degenerative when histologically and/or biochemically normal tissue is altered in such a way that the tissue no longer functions properly. Degenerative tissue remodeling may occur progressively in patients suffering from congestive heart failure or atrial fibrillation. In those patients, the resulting remodeling adversely affects the heart's performance and exacerbates the deteriorating condition of the heart. Tissue remodeling is beneficial when a histologically and/or biochemically abnormal tissue is reverted to a more normal histology and/or biochemistry.

Recently, one aspect of degenerative remodeling due to the progression of CHF has been identified as the breakdown in the collagen of the extra-cellular matrix. The extra-cellular matrix is the external structure between the cells in the heart that primarily consists of a matrix of type I collagen and fibrils. This matrix is connected to the cytoskeletal myofibrils within the myocardial cells. The matrix provides tensile strength to the tissue, governs the tissue's stiffness, and preserves the alignment of the myocardial cells. Abnormalities in the matrix's composition and concentration during dilation, hypertrophy and ischemic injury inhibit the function of the heart and may lead to heart failure.

Endogenous factors regulate the breakdown and/or reestablishment of collagen and other extra-cellular matrix components. These endogenous factors are diverse and their functions and structures are the subject of much research. The endogenous factors include a family of enzymes known as the matrix metalloproteinases. The matrix metalloproteinases catalyze a reaction breaking down the extra-cellular matrix. The enzymatic activity of the matrix metalloproteinases is countered by a set of proteins known as the tissue inhibitors of the matrix metalloproteinases (TIMPs). The TIMPs inhibit the enzymatic activity of the matrix metalloproteinases. The matrix metalloproteinase:TIMP ratio is typically around 1.1:1.0 in a normal heart. The ratio may be around 6:1 or 7:1 by the end stage of CHF. Research has shown that the interruption of matrix metalloproteinases with pharmaceutical agents reduces chamber dilation in animal models for CHF. Relatedly, this research has shown an overall increase in the collagen content due to the treatments.

In addition, the inhibition of matrix metalloproteinases and, presumably, the subsequent increase in collagen have been shown to result in the beneficial remodeling of treated diseased hearts. Interruption of matrix metalloproteinases with drug therapy has been shown to reduce chamber dilation in CHF animal models. However, drug therapy for inhibiting matrix metalloproteinases may present potentially serious problems. The systemic inhibition of the matrix metalloproteinases has been found to produce a variety of side effects, such as joint and muscle pain. Therefore, a need exists for a therapy that specifically targets the desired tissue or organ to be treated.

Another aspect of degenerative remodeling is ischemic cardiomyopathy. In ischemic cardiomyopathy, a loss of blood flow or ischemia to a portion of the heart muscle causes not just weakness or scarring to that portion, but subsequently a progression to chamber dilation and failure. The loss of blood flow may be the result of arteriosclerosis, other cardiac diseases, or injury, which can result in a partial or complete blocking of blood flow to a region of the heart. The limited blood flow may result in localized tissue death known as an infarction. The presence of an infarction weakens contraction in that region and therefore degrades the heart's performance. To compound the problem, the myocardial tissue adjacent to the infarction typically receives a reduced blood flow and, therefore, exhibits reduced contractility. The zone receiving the reduced blood flow is known as an ischemic zone. The ischemic zone further inhibits the hearts ability to contract. Further, the elevation of matrix metalloproteinases, reduction in TIMPs, and consequent degradation of collagen may play an additional role in ischemic cardiomyopathy. To improve cardiac output in patients with ischemic cardiomyopathies, there is a need to re-establish blood flow to the ischemic zones.

Re-establishing blood flow to the ischemic zone has been shown to improve cardiac function. Re-establishing blood flow may be accomplished through angiogenesis in which the body generates additional blood vessels in a particular region. Prior methods for re-establishing blood flow and rehabilitating the heart frequently involved invasive surgery such as bypass surgery or angioplasty. Other methods have used lasers to bore holes through the infarctions and ischemic zones to promote blood flow. These surgeries are complicated and dangerous. Therefore, a need exists for a safe non-invasive method for re-establishing blood flow.

As alternatives to surgery, various chemical and biological agents have been developed that promote angiogenesis. Genetic engineering has played a significant role in the development of many of these new agents. However, in practice, direct injection of these angiogenic agents fails to specifically target the ischemic zone. Further, injection of genetic material within a vector is a more biologically complex process and frequently suffers from a low transfection efficiency. In addition, the introduction of xenobiotics compounds can be dangerous. The compound itself may be toxic, virulent and/or allergenic. Therefore, a need exists for a therapy for promoting angiogenesis that is efficient and does not introduce xenobiotics into a patient. In addition, many of the drugs prescribed for CHF patients are primarily for palliative or symptomatic relief. These drugs typically do not treat the underlying disease process of CHF and their use frequently results in serious or prohibitive side effects. Further, the drugs are typically administered systemically and therefore, impact the entire body not just the organ or tissue to be treated. Therefore, a need exists for a therapy capable of promoting overall remodeling without inducing unwanted side effects.

Atrial fibrillation is another serious condition in which degenerative tissue remodeling also plays a significant role. As in CHF and coronary ischemic disease, early theories on the cause of atrial fibrillation suggested that its causes may be multi-factorial, but the onset of degenerative tissue remodeling exacerbates atrial fibrillation.

The promotion of healing with electric current stimulation has been recognized in medicine for many years. Most commonly, electricity is used to promote bone union in fractures that have proven refractory to normal healing. The devices used have directly applied the current to the skin over the fracture. Alternatively, other devices use pulsed electromagnetic fields (PEMF) that do not require direct skin contact to promote healing.

Electrical stimulation of cardiac tissues has also been utilized to treat various conditions of the heart. Pacemakers provide electrical stimulation above the contraction threshold to treat various arrhythmias. Further, sub-threshold stimulation currents have been used to extend the cardiac tissue's refractory period in the treatment of tachycardia and to increase contractility in the cardiac muscle. However, sub-threshold stimuli have not been broadly applied to the heart and adjacent blood vessels to promote healing and tissue remodeling.

Providing electric current stimulation of ischemic zones on the heart has recently been shown to promote angiogenesis and further, electric current stimulation has been shown to increase collagen type I production in cultured cells. However, directly or indirectly applying electrical stimulation to the heart can be dangerous. There is a risk of inducing a depolarization of the cardiac tissue resulting in an unwanted cardiac contraction. Further, there is a risk of inducing a life-threatening arrhythmia. Therefore, a need exists to provide a method and apparatus that reduces the risks of providing an electrical stimulation to the heart to promote angiogenesis, to increase collagen type I production, to prevent the breakdown or degradation of extra-cellular matrix proteins, and to promote other aspects of beneficial remodeling.

One problem not addressed by prior methods is the inability to accurately assess the field strength generated in the region of the heart. Significant variation in body types, conductivity profiles and stimulation thresholds exist between patients. A particular stimulus level may be safe when applied to one patient, and yet that same stimulus may evoke an unwanted reaction from another patient. Thus, a need exists for a method and apparatus for measuring the field strength of a therapeutic current. Another problem is the artifact created by an applied stimulus, which may disrupt the sensing and activation of an implanted pacing or defibrillation device. The disruption could result in stimulation at a high-risk portion of the cardiac cycle, or an undesirable or unnecessary defibrillation shock. Thus, a need also exists for a method and apparatus that reduce the likelihood for disruption of an implanted pacing or defibrillation device.

The apparatus and method of the present invention meet the above needs and provide additional improvements and advantages that will be evident to those skilled in the art upon review of the specification and figures.

SUMMARY OF THE INVENTION

The apparatus and method use therapeutic current stimulation that optimizes safety and therapeutic benefit in treating cardiac tissue. The apparatus for remodeling a heart includes a first electrode, a second electrode, a current generator, and a controller. The apparatus may further include one or more sensors. The sensors being configured to measure field strength from the electrodes and may also monitor the cardiac cycle. The sensors may be implanted in or on the heart or they may be positioned within the esophagus or trachea. The controller is configured to regulate the output from the current generator to maintain the field strength below the heart's depolarization threshold. The sensors may further monitor the depolarization of the heart and the controller may synchronize the therapeutic electrical stimulation from the current generator with a cycle of the heart. The controller's synchronization may apply the electrical stimulation during the refractory period of the cardiac cycle. Alternatively or in addition, the sensor may monitor the field strength at a location in or near the heart generated between the first electrode and the second electrode. When monitoring field strength, the controller maintains the sub-threshold therapeutic electrical stimulation from the current generator at a level below a stimulation threshold of the heart. A cardiac defibrillator may also be incorporated as an integral part of the device. Further, the apparatus may be integral with a cardiac pacemaker. In addition, the apparatus may utilize the pacemaker's or defibrillator's electrodes implanted within the patient to eliminate the need for additional implantation surgery.

The method of the present invention provides cardiac therapy. The method includes applying a stimulus to the heart and measuring the field strength generated by applying the stimulus to maintain the field strength below the heart's depolarization threshold and/or sensing the cardiac cycle to establish the varying depolarization threshold and applying a varying stimulus below the threshold for the particular points within the cardiac cycle.

The invention provides many advantages. The present invention provides the heart with a safe therapeutic current to promote healing of diseased or inflamed tissue. The invention mitigates the concerns relating to the application of therapeutic current to the heart, including but not limited to the concerns of uncontrolled or dangerous current level and the possible dangerous asynchronous application of current with respect to the cardiac cycle. The apparatus and method allow for long-term treatment for beneficial remodeling of the heart while minimizing the risk of damaging tissue.

DETAILED DESCRIPTION OF THE INVENTION

The present invention is described generally as a therapy for promoting remodeling of a patient's heart. Those skilled in the art will recognize the improvements and advantages conferred by the present invention in the treatment of heart disease and heart failure, the specific etiologies including, but not limited to, ischemic cardiomyopathy, idiopathic dilated cardiomyopathy, other cardiomyopathies, myocarditis and atrial fibrillation.

Figure 1:
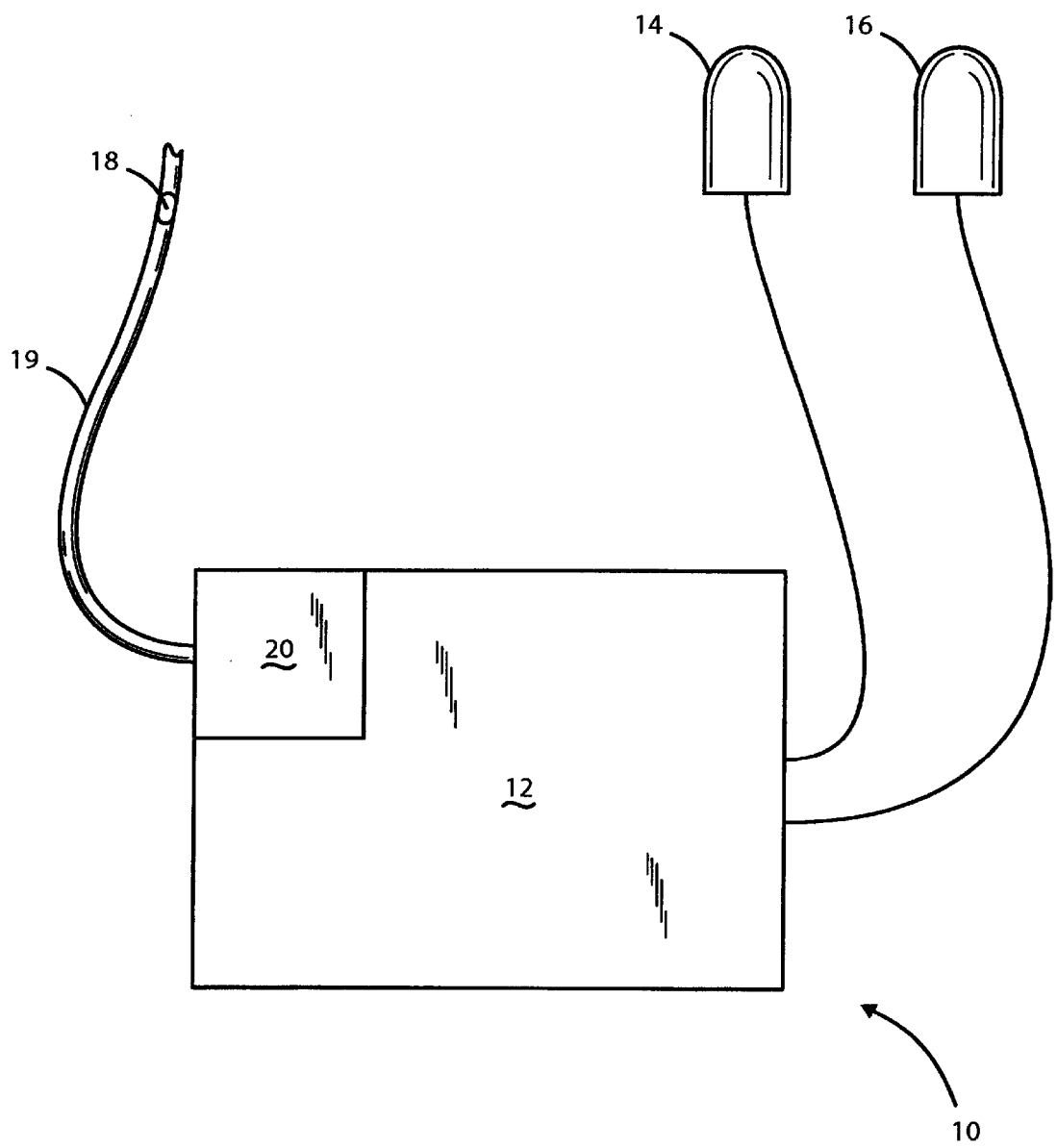
FIG. 1 illustrates an apparatus in accordance with the present invention.

An apparatus 10 in accordance with the present invention is shown in FIG. 1. Apparatus 10 includes a current generator 12, a first electrode 14, a second electrode 16, a sensor 18, and a controller 20. First drive electrode 14 and second drive electrode 16 are configured to be implanted in a chamber of the heart or within the coronary vessels, or are configured to be secured on or near the heart. Typically, the electrodes are connected to current generator 12 by a conductive wire. Current generator 12 is configured to provide a sub-threshold stimulus through heart tissue positioned between first electrode 14 and second electrode 16. Current generator 12 allows the adjustment of one or more parameters of the output current. One or more sensors 18 are configured to sense the electric field strength in or near the heart resulting from current generator 12. Sensors 18 may also sense the depolarizations of the heart. A typical sensor configuration may include a pair of endocardial sensing electrodes. Sensors 18 may be implantable, such that the sensors may be positioned in, on or around the heart, shown in FIG. 3. Alternatively, the sensors may be positioned within a patient's esophagus or trachea. Sensors 18 are in communication with controller 20, either directly by wire or through a telemetry link, to confer information indicative of the field strength and may also confer information regarding the cardiac cycle. Further, sensor 18 and/or electrodes 14 and 16 may be integral with a cardiac lead attached to a conventional cardiac pacemaker or defibrillator. The cardiac pacemaker/defibrillator will typically house a battery power source and electronics. Controller 20 is also in communication with current generator 12, either directly by wire or through a telemetry link. Controller 20, shown in FIG. 1, is integral with current generator 12 for exemplary purposes only. Controller 20 is configured to adjust at least one of the parameters of the sub-threshold electrical stimulus output from the current generator and/or to switch the current generator on and off based on input from sensors 18.

Figure 2:
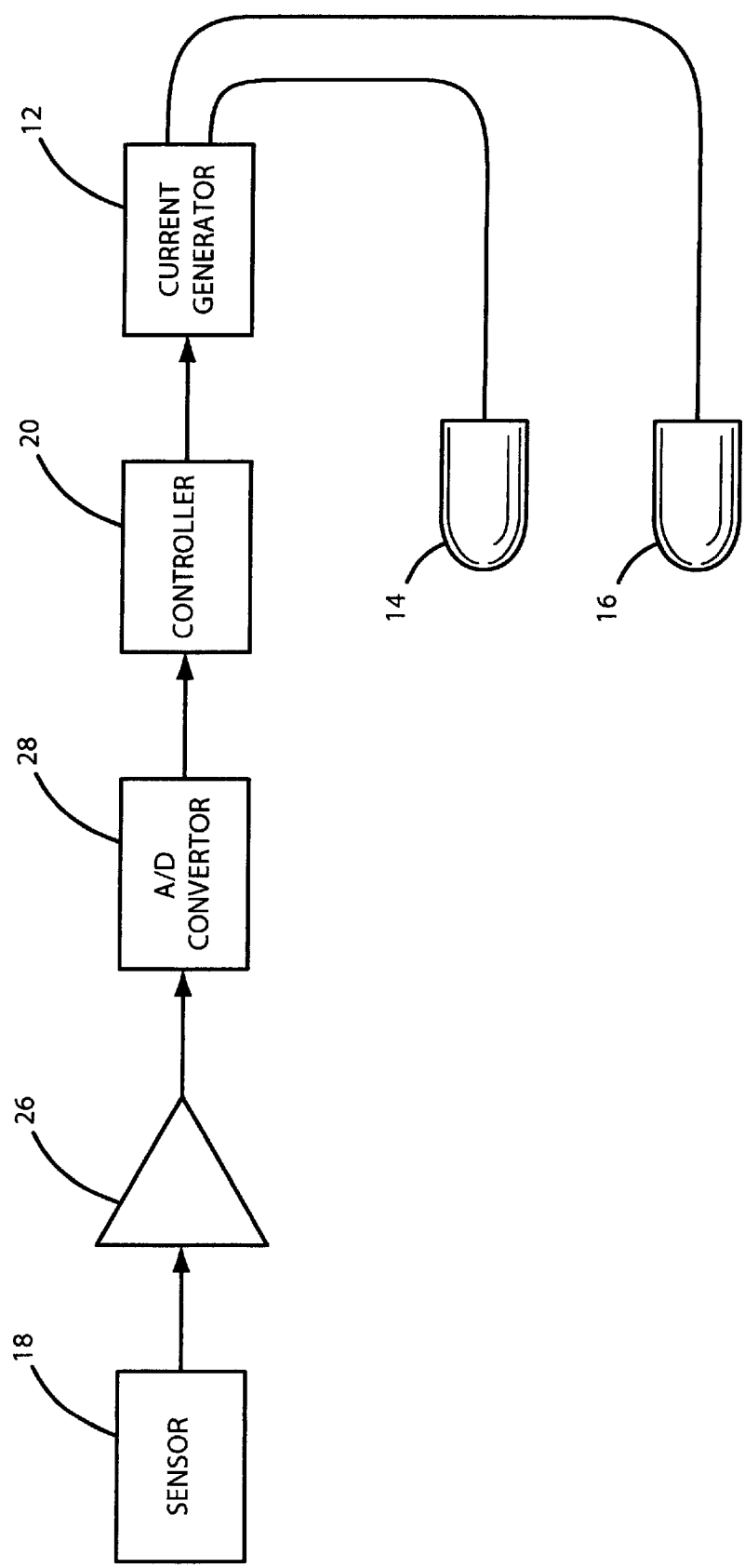
FIG. 2 illustrates a block diagram of an embodiment of an apparatus in accordance with the present invention.

The embodiment shown in FIG. 2 includes a sensor 18, an amplifier 26, an analog to digital (A/D) converter 28, a controller 20, a current generator 12, a first drive electrode 14 and a second drive electrode 16. The configuration shown in FIG. 2 permits the amplification and digital conversion of the analog data sensed by sensor 18. The digital data is received and analyzed by controller 20. Controller 20 determines the appropriate therapeutic current based on the sensed data and the particular therapy being implemented. Controller 20 then communicates a controlling signal to current generator 12. Based on the controlling signal, current generator 12 applies the appropriate current levels, frequency output and/or timing to first drive electrode 14 and second drive electrode 16. Sensor 18 may be secured to an endocardial lead and positioned in the right ventricle of the heart, or it may be part of a coronary lead or epicardial lead. In such a configuration, implanted sensor 18 senses cardiac cycle and/or field strengths of signals resulting from the intrinsic electrical activity and therapeutic current, and these signals are provided to controller 20 through the signal path of amplifier 26 and A/D converter 28. This information allows controller 20 to maintain the current from current generator 12 at safe but efficacious levels.

Figure 3:
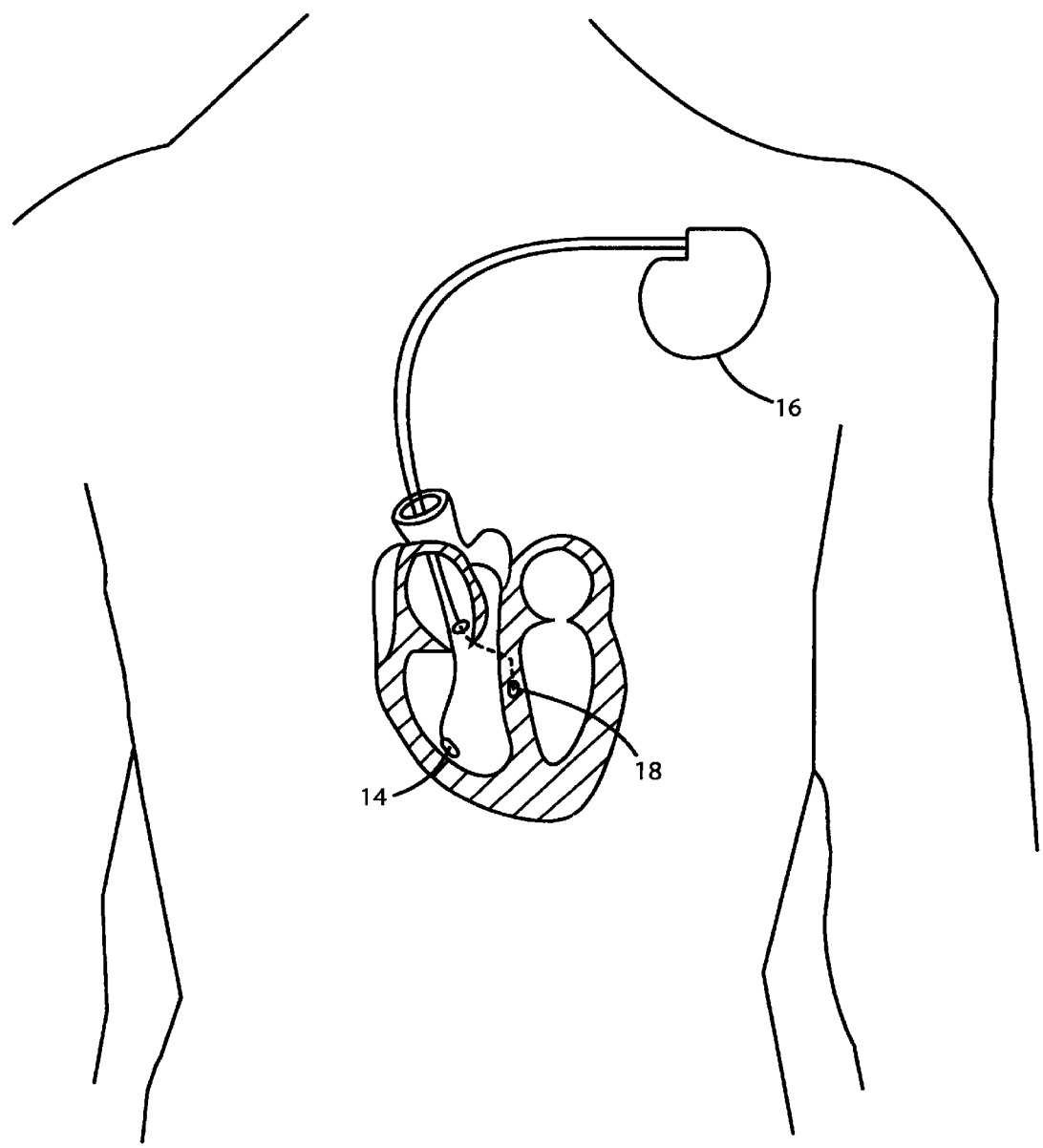
FIG. 3 illustrates an embodiment of an apparatus in accordance with the present invention having an electrode and sensor implanted in the heart.

As illustrated in FIG. 3, first electrode 14 and second electrode 16 may be configured for placement in a manner similar to implantable defibrillator electrodes. First electrode 14 utilizes the defibrillation electrode of a right ventricular endocardial lead. The defibrillation electrode affords a broad distribution of current. Electrode 16 is integral with the housing, or 'can' of the implanted device, which houses the electronics such as the controller 20 and current generator 12. The sub-threshold current flow for the invention will thus flow in a broad path from electrode 14 to the implanted can electrode 16, the can being typically implanted in the left pectoral region. Thus the septum, left ventricle and left atrium will incur a fairly uniform density in this embodiment. In FIG. 3, an additional pair of electrodes may comprise the sensor 18. The sensor is shown on a catheter placed in the coronary sinus for exemplary purposes.

Figure 4:
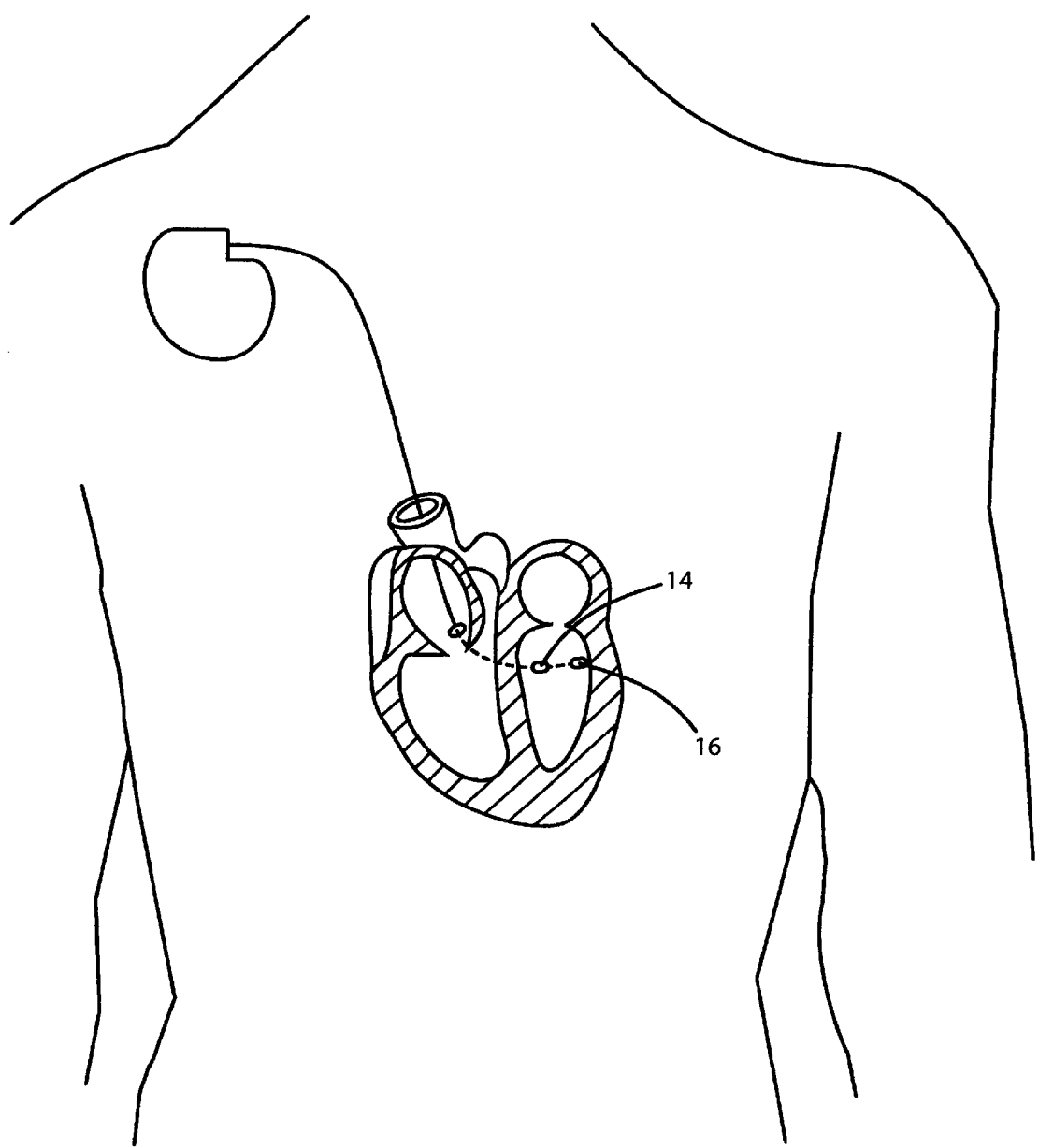
FIG. 4 illustrates another embodiment of an apparatus in accordance with the present invention having a first and second electrode implanted within the heart through a coronary vein access.

Alternatively, electrodes 14 and 16 may be positioned on or in the heart so that when a current flows between the electrodes 14 and 16 the current passes through the region of the heart requiring therapy. For example, a lead may include a pair of electrodes spaced about 2 centimeters apart as shown in FIG. 4. The lead is shown with a right atrial access, passing through the coronary sinus, with the electrodes 14 and 16 positioned so that they are near an ischemic region in the posterior left ventricle, where therapy is required. Only a significant current density would be realized in the required area in this embodiment.

Therapy using apparatus 10 may utilize a broad range of currents. The particular current used may be optimized to preferentially stimulate a cell-initiated angiogenic response, to promote collagen type I production and/or to stimulate another aspect of beneficial remodeling. Current generator 12 typically provides drive currents in the range of microamperes to milliamperes. The drive current may be between 10 microamperes to 10 milliamperes although higher or lower drive currents may be used. As discussed above, since the field strength resulting from the current in or near the heart is assessed, and the drive current needed to achieve a given field strength will vary from patient to patient.

Apparatus 10 may utilize either a direct current (DC) or an alternating current (AC). When AC current is used, a wide range of frequencies may be utilized with particular frequencies being tailored to particular therapies. Typically, the sinusoidal frequencies used are between 2 Hz and 200 Hz, although higher sinusoidal frequencies in the range of tens of kilohertz may be utilized. For example, the application of a frequency of around 20 hertz has been shown to be efficacious in increasing expression of Type 1 collagen, while higher frequencies have been shown to be efficacious in promoting angiogenesis. Alternatively, pulsed fields have proven efficacious in promoting angiogenesis. Pulsed waveforms typically result in higher frequency components. When lower frequencies are utilized the control algorithm implemented by controller 20 compensates for the lower depolarization thresholds resultant from the lower frequencies.

In one embodiment for current application, the therapeutic current is applied continuously at a constant level below stimulation threshold without regard to the heart's cycle. A field strength is selected that is below the stimulation threshold of the myocardial tissue. For example, using the 20 Hz sinusoidal waveform, a 200 microamperes/cm$^2$ current density may provide an electric field strength within the heart tissue of around 80 mV/cm, given typical values for myocardial resistivity.

In another embodiment for current application, the stimulus amplitude may be dynamically modified with respect to the cardiac cycle. Typically, the current density may be relatively large during the refractory period and drop to a sub-threshold level outside of the heart's refractory period. Thus, the heart's cycle is monitored as described above. Upon detection of a depolarization event, the current density is increased during a predetermined window. At the conclusion of a window, typically 200 milliseconds, the current is then lowered to a pre-determined level below the depolarization threshold of the subject heart.

It is recognized that substantial current drain may be required for this invention relative to conventional implantable devices such as pacemakers and defibrillators. Well known means of transcutaneous re-charging of the implantable battery may be used to support this invention. A separate re-chargeable battery may be used, so as to leave the critical pacing and defibrillator functions independent of current drain from this invention.

Sensors 18 may monitor the electric field strength created by current generator 12 and may also monitor the patient's intrinsic heart rhythm. This monitoring facilitates the safe application of the therapeutic current. The sensed field waveform and/or the patient's intrinsic cardiac biopotentials are communicated to controller 20 to regulate current generator 12. Thus, apparatus 10 mitigates the danger of uncontrolled or dangerous current levels and/or asynchronous application of therapeutic current with respect to the cardiac cycle. The following embodiments for sensor 18 are provided for exemplary purposes. Upon review of the present disclosure, those skilled in the art will recognize that a variety of additional sensor configurations may be used to monitor the depolarization of the heart and/or to measure field strength in accordance with the present invention.

In one embodiment, sensor 18 is a pair of electrodes secured to a cardiac lead, as shown in FIG. 3. The lead is connected to a pacemaker or defibrillator lead system. The electrodes are configured to monitor the field strength generated by current generator 12. To measure the field strength, the electrodes may be aligned substantially along a line or axis formed between the two drive electrodes. Typically, the axis connecting sensors 18 lie within 30 degrees of the drive electrodes' axis. Alternatively, if sensors 18 are at any given known or measured angle with respect to the drive electrode axis, the maximum magnitude of field strength can be calculated by dividing the measured value by the cosine of this angle. The electrodes of sensor 18 are electrically coupled to amplifier 26. Amplifier 26 is configured with a bandwidth suitable to recover the frequency of the therapeutic current being administered. The amplified signal is converted to a digital signal by the A/D converter 28. A/D converter 28 then communicates the signal to controller 20. The therapeutic waveform may be recovered and separated from any noise and biopotentials in the signal using synchronous demodulation or other techniques that will be recognized by those skilled in the art. The peak or RMS value of the signal received may be calculated using appropriate gain factors to account for the degree of amplification.

The voltage value may then be divided by the sense electrode spacing to calculate the electric field strength. If the sensor is in the blood, the myocardial field strength may be calculated by multiplying the blood pool field strength by about 3, to account for the resistivity differences of blood and the myocardium. This is valid under conditions of uniform current density, and noting the current continuity between the tissue and blood conductors.

In another embodiment, a sensor 18 is a pair of electrodes secured to a deflectable electrophysiology catheter. Sensor 18 electrodes are introduced into a chamber of the heart. The deflectable catheter may be oriented until a maximum in field strength is measured between the electrodes. The orientation with maximum field strength occurs when the axis between the sensor electrodes aligns with the vector of the electric field. The vector of the electric field is coincident with the axis between the patch electrodes 14 and 16. The use of a deflectable catheter facilitates a one-time calibration of field strength as a function of drive current for a particular patient. The calibration may then be used in subsequent applications of the therapeutic method to the patient, without the need for further catheterization.

In yet another embodiment, sensor 18 is a pair of electrodes positioned on a trans-esophageal probe. The sensor electrodes are inserted through the esophagus to a position adjacent the patient's heart. The trans-esophageal probe is oriented with a first sensor electrode anterior, or facing the chest of the patient, and the second sensor electrode posterior, or facing the patient's back. The probe may be positioned in the cardiac region to make a field measurement, and as such obviates the need for more invasive catheterization.

In use, sensors 18 may be used to initially measure the field strength, to continually measure the field strength or to periodically measure the field strength for a particular patient. For example, the field strength may be established using an independent sensing apparatus in a clinical setting. To establish the threshold, the applied current may be incrementally changed to determine the depolarization threshold for a particular patient's heart. This type of 'threshold testing' may emulate amplitude step-up and step-down protocols as will be recognized by those skilled in the art. The cardiac sensing will indicate ectopic or untoward stimulation. The identification of the ectopic or untoward stimulation will allow the therapeutic current amplitude and frequency to be set below stimulation threshold with sufficient safety margin. Furthermore, the resultant threshold field strength may be assessed. Continuous or periodic monitoring of the field strength after the initial therapeutic current level has been set will allow controller 20 to adjust the value during therapy. For example, if electrodes 14 and 16 are repositioned, the current density through the heart may change significantly, if the applied current remained constant. In an unmonitored situation, this could either pose a stimulation danger, or result in reduced therapy, but with the benefit of this invention, the applied current may be adjusted dynamically.

The present invention has been described in considerable detail in order to comply with the patent statutes and to provide those skilled in the art with the information needed to apply the novel principles and to construct and use such components to practice the invention. However, upon review of this disclosure, those skilled in the art will recognize that the invention can be practiced with specifically different equipment and devices, and that various modifications, both to the apparatus and method, can be accomplished without departing from the scope of the present invention.

What is claimed is:

1. An apparatus for remodeling a heart of a patient, comprising:
    a first electrode adapted to be disposed on the patient;
    a second electrode adapted to be disposed on the patient;
    a current generator electrically coupled to the first electrode and the second electrode, wherein the generator generates a current between the first electrode and the second electrode to confer a sub-threshold therapeutic stimulus on the heart; and
    at least one sensor operatively coupled to the current generator and adapted to monitor the field strength of the therapeutic stimulus in or near the heart generated between the first electrode and the second electrode.

2. An apparatus, as in claim 1, further comprising a controller in communication with the sensor, the controller providing an output to regulate the current generator.

3. An apparatus, as in claim 2, wherein the controller maintains the sub-threshold therapeutic stimulus from the current generator below a depolarization threshold of the heart.

4. An apparatus, as in claim 1, wherein at least one of the sensor, the first electrode, and the second electrode is adapted to be positioned within an esophagus of the patient.

5. An apparatus, as in claim 1, wherein the sensor is an implantable sensor.

6. An apparatus, as in claim 5, wherein the sensor is adapted to be disposed within the heart.

7. An apparatus, as in claim 1, further comprising a cardiac defibrillator disposed in a hermetically sealed housing along with said current generator.

8. An apparatus, as in claim 1, further comprising a cardiac pacemaker disposed in a hermetically sealed housing along with said current generator.

9. An apparatus for remodeling a heart, comprising:
    a first means for forming an electrical connection with the heart;
    a second means for forming an electrical connection with the heart;
    a means for generating an electric current between the first means for forming an electrical connection and the second means for forming an electrical connection, wherein the means for generating an electric current generates a sub-threshold therapeutic stimulus passing between the first means for forming an electrical connection and the second means for forming an electrical connection to the heart; and
    a means for sensing the field strength of the therapeutic stimulus operatively coupled to said means for generating.

10. An apparatus, as in claim 9, further comprising a means for controlling the output from the means for generating an electric current to maintain the field strength of the therapeutic stimulus below a depolarization threshold of the heart.

* * * * *